US008822547B2

(12) United States Patent
Snyder et al.

(10) Patent No.: US 8,822,547 B2
(45) Date of Patent: Sep. 2, 2014

(54) HYDROALCOHOLIC GEL COMPOSITIONS FOR USE WITH DISPENSERS

(75) Inventors: Marcia Snyder, Stow, OH (US); Carol A. Quezada, Canal Fulton, OH (US)

(73) Assignee: GOJO Industries, Inc., Akron, OH (US)

( * ) Notice: Subject to any disclaimer, the term of this patent is extended or adjusted under 35 U.S.C. 154(b) by 543 days.

(21) Appl. No.: 12/739,033

(22) PCT Filed: Oct. 29, 2008

(86) PCT No.: PCT/US2008/081502
§ 371 (c)(1),
(2), (4) Date: Apr. 21, 2010

(87) PCT Pub. No.: WO2009/058802
PCT Pub. Date: May 7, 2009

(65) Prior Publication Data
US 2011/0144214 A1    Jun. 16, 2011

Related U.S. Application Data

(60) Provisional application No. 60/983,856, filed on Oct. 30, 2007.

(51) Int. Cl.
*A61K 31/045* (2006.01)
*A61K 8/37* (2006.01)
*A61K 8/81* (2006.01)
*A61Q 19/00* (2006.01)
*A61K 8/04* (2006.01)
*A61K 8/34* (2006.01)

(52) U.S. Cl.
CPC . *A61K 8/042* (2013.01); *A61K 8/37* (2013.01); *A61K 8/8147* (2013.01); *A61Q 19/00* (2013.01); *A61K 2800/87* (2013.01); *A61K 8/375* (2013.01); *A61K 8/34* (2013.01)
USPC ........................................................ 514/724

(58) Field of Classification Search
CPC ......... A61K 8/042; A61K 8/37; A61K 8/375; A61K 8/8147
See application file for complete search history.

(56) References Cited

U.S. PATENT DOCUMENTS

| 3,069,319 | A | | 12/1962 | Stearns |
| 3,954,960 | A | | 5/1976 | Valan |
| 4,525,348 | A | * | 6/1985 | Arizono et al. ............... 514/291 |
| 4,933,177 | A | | 6/1990 | Grollier et al. |
| 4,956,170 | A | * | 9/1990 | Lee ........................... 514/772.1 |
| 4,961,921 | A | | 10/1990 | Chuang et al. |
| 5,167,950 | A | | 12/1992 | Lins |
| 5,266,598 | A | | 11/1993 | Ninomiya et al. |
| 5,340,570 | A | * | 8/1994 | Wong et al. ................. 424/70.12 |
| 5,714,135 | A | * | 2/1998 | Lee et al. ................... 424/70.11 |
| 5,985,294 | A | | 11/1999 | Peffly |
| 6,096,297 | A | | 8/2000 | Jones et al. |
| 6,096,349 | A | * | 8/2000 | Petri et al. ..................... 424/616 |
| 7,199,090 | B2 | | 4/2007 | Koivisto et al. |
| 7,566,460 | B2 | | 7/2009 | Asmus et al. |
| 2005/0220745 | A1 | * | 10/2005 | Lu .............................. 424/70.11 |
| 2007/0065385 | A1 | | 3/2007 | Porter |
| 2007/0082039 | A1 | | 4/2007 | Jones, Jr. et al. |
| 2007/0258934 | A1 | * | 11/2007 | Bui et al. .................. 424/70.11 |
| 2007/0275929 | A1 | | 11/2007 | Fuls et al. |

FOREIGN PATENT DOCUMENTS

| EP | 0796610 A1 | 9/1997 |
| EP | 1764135 A1 | 3/2007 |
| JP | 244010/92 | 9/1992 |
| JP | 2002-167315 | 6/2002 |
| JP | 2005-187411 | 7/2005 |
| WO | WO 97/00668 A1 | 1/1997 |
| WO | WO 9939687 A1 | 8/1999 |
| WO | WO 03003998 A1 | 1/2003 |
| WO | 2007068699 | 6/2007 |

OTHER PUBLICATIONS

International Search Report and Written Opinion of the International Searching Authority, International Appl No. PCT/US2008/081502 dated Dec. 16, 2010; 13 pages.
Pepe et al., International Cosmetic Ingredient Dictionary and Handbook, Ninth Edition, vol. 1, 2002 (Title page, p. 486, page bearing definition for PPG-2 Myristyl Ether Propionate (pg. number unknown)).

\* cited by examiner

*Primary Examiner* — Sean Basquill
(74) *Attorney, Agent, or Firm* — Renner, Kenner, Greive, Bobak, Taylor & Weber Co. LPA

(57) ABSTRACT

A hydroalcoholic gel composition includes greater than about 40 weight percent of an alcohol, based upon the total weight of the alcoholic composition, a polyacrylate thickener, and an ester plug-preventing agent. The composition is suitable for use in dispensers, and exhibits reduced mis-directed output when the dispenser is actuated.

30 Claims, No Drawings

HYDROALCOHOLIC GEL COMPOSITIONS FOR USE WITH DISPENSERS

RELATED APPLICATIONS

This application claims the benefit of U.S. Provisional Application No. 60/983,856 filed on Oct. 30, 2007. The application is expressly incorporated herein by reference.

TECHNICAL FIELD

This invention relates to hydroalcoholic gel compositions for use with dispensers, wherein the frequency of mis-directed dispenser output is reduced when the hydroalcoholic gel compositions include a plug-preventing additive.

BACKGROUND OF THE INVENTION

Personal care and sanitizing compositions are often formulated as hydroalcoholic gels. Frequently, these products are provided in dispensers. Dispenser outlets such as nozzles can become clogged or partially blocked over time, due to the coagulation of gel creating a deposit on the nozzles. The clogged nozzle then causes mis-direction of the product when the dispenser is next used. Instead of dispensing product directly into the user's hand, product shoots from the clogged nozzle in a sideways fashion. Mis-directed product may hit walls, clothing, the floor, and can cause damage to these articles or areas.

Therefore there remains a need for hydroalcoholic gel compositions that exhibit a reduced occurrence of clogging of dispenser nozzles.

SUMMARY OF THE INVENTION

One or more embodiments provide a method of reducing the formation of coagulated gel deposits, the method comprising the steps of combining a $C_{1-4}$ alcohol, an effective amount of a polyacrylate thickener; and a plug-preventing additive to form a dispensable gel composition; wherein the plug-preventing additive comprises an ester having from two to six ester groups or a polymeric ester that includes at least one ester group; and wherein said composition comprises at least about 40 wt. % of said alcohol and less than about 1 wt. % of fatty alcohol, petrolatum, mineral oil, or mixtures thereof, all based upon the total weight of the dispensable gel composition, and storing the dispensable gel in a pump-type dispenser that is activated on a periodic basis, wherein the formation of coagulated gel deposits is reduced when compared to a dispensable gel that does not include the plug-preventing additive.

One or more embodiments of this invention further provide a method of reducing the frequency of mis-directed output from a gel dispenser, the method comprising the steps of combining a $C_{1-4}$ alcohol, an effective amount of a polyacrylate thickener; and a plug-preventing additive to form a dispensable gel composition; wherein said plug-preventing additive comprises an ester having from two to six ester groups or a polymeric ester that includes at least one ester group; and wherein said composition comprises at least about 40 wt. % of said alcohol and less than about 1 wt. % of fatty alcohol, petrolatum, mineral oil, or mixtures thereof, all based upon the total weight of the dispensable gel composition, and storing the dispensable gel in a pump-type dispenser that includes an outlet and that is activated on a periodic basis, wherein the frequency of mis-directed output is reduced when compared to a dispensable gel that does not include the plug-preventing additive.

One or more embodiments of this invention still further provide a gel composition comprising at least about 60 wt. % of a $C_{1-4}$ alcohol, based upon the total weight of the gel composition, an effective amount of a polyacrylate thickener, an ester plug-preventing additive that includes from two to six ester groups or a polymeric ester that includes at least one ester group, and less than about 1 wt. % of fatty alcohol, petrolatum, mineral oil, or mixtures thereof, based upon the total weight of the gel composition.

DETAILED DESCRIPTION OF ILLUSTRATIVE EMBODIMENTS

In one or more embodiments, dispensable hydroalcoholic gel compositions of the present invention include a hydroalcoholic carrier, a polyacrylate thickener, and a plug-preventing additive. In one or more embodiments, the hydroalcoholic carrier includes water and alcohol.

In one embodiment, the alcohol is a lower alkanol, i.e. an alcohol containing 1 to 4 carbon atoms. Typically, these alcohols have antimicrobial properties. Examples of lower alkanols include, but are not limited to, methanol, ethanol, propanol, isopropanol, butanol, isobutanol, tertiary butanol, and mixtures thereof. In one embodiment, the alcohol comprises ethanol.

Generally, the hydroalcoholic gel composition comprises an amount of alcohol of at least about 40 weight percent (wt. %), based upon the total weight of the hydroalcoholic gel composition. In one embodiment, the hydroalcoholic gel composition comprises at least about 45 weight percent alcohol, in another embodiment, the hydroalcoholic gel composition comprises at least about 50 weight percent alcohol, and in yet another embodiment, the hydroalcoholic gel composition comprises at least about 60 weight percent alcohol, based upon the total weight of hydroalcoholic gel composition. More or less alcohol may be required in certain instances, depending particularly on other ingredients and/or the amounts thereof employed in the composition. In certain embodiments, the hydroalcoholic gel composition comprises from about 40 weight percent to about 98 weight percent alcohol, in other embodiments, the hydroalcoholic gel composition comprises from about 45 weight percent to about 95 weight percent of alcohol, in yet other embodiments, the hydroalcoholic gel composition comprises from about 50 weight percent to about 90 weight percent of alcohol, and in still other embodiments, the hydroalcoholic gel composition comprises from about 60 weight percent to about 80 weight percent of alcohol, based upon the total weight of the hydroalcoholic gel composition.

The hydroalcoholic gel composition may include a mixture of $C_{1-9}$ alkanols. In one or more embodiments, the hydroalcoholic gel composition includes a mixture of one or more $C_{1-4}$ alkanols and one or more $C_{5-9}$ alkanols. The mixture may include primary, secondary, or tertiary alcohols.

The hydroalcoholic gel may be thickened with polyacrylate thickeners such as those conventionally available and/or known in the art. Examples of polyacrylate thickeners include carbomers, acrylates/C10-30 alkyl acrylate crosspolymers, copolymers of acrylic acid and alkyl (C5-C10) acrylate, copolymers of acrylic acid and maleic anhydride, and mixtures thereof.

In one or more embodiments, the polymeric thickener includes from about 0.5% to about 4% by weight of a cross-linking agent. Examples of cross-linking agents include the polyalkenyl polyethers.

Commercially available polymers of the polyacrylate type include those sold under the trade names Carbopol®, Acrysol® ICS-1, Polygel®, Sokalan®, Carbopol® 1623, Carbopol® 695, Ultrez 10, and Polygel® DB.

In one or more embodiments, the composition of the present invention includes an effective amount of a polymeric thickener to adjust the viscosity of the hydroalcoholic gel to a viscosity range of from about 1000 to about 65,000 centipoise. In one embodiment, the viscosity of the hydroalcoholic gel is from about 5000 to about 35,000, and in another embodiment, the viscosity is from about 10,000 to about 25,000. The viscosity is measured by a Brookfield RV Viscometer using RV and/or LV Spindles at 22° C.+/−3° C.

As will be appreciated by one of skill in the art, the effective amount of thickener will vary depending upon a number of factors, including the amount of alcohol and other ingredients in the hydroalcoholic gel composition. In one or more embodiments, an effective amount of thickener is at least about 0.01 wt. %, based upon the total weight of the hydroalcoholic gel composition. In other embodiments, the effective amount is at least about 0.02 wt. %, in yet other embodiments at least about 0.05 wt. %, and it still other embodiments, at least about 0.1 wt. %. In one embodiment, the effective amount of thickener is at least about 0.5 wt. %, and in another embodiment, at least about 0.75 wt. %, based upon the total weight of the hydroalcoholic gel. In one or more embodiments, the compositions according to the present invention comprise up to about 10% by weight of the total composition of a polymeric thickener. In certain embodiments, the amount of thickener is from about 0.01 to about 1 wt. %, in another embodiment, from about 0.02 to about 0.4 wt. %, and in another embodiment, from about 0.05 to about 0.3 wt. %, based upon the total weight of the hydroalcoholic gel. In one embodiment, the amount of thickener is from about 0.1 to about 10 wt. %, in another embodiment from about 0.5% to about 5% by weight, in another embodiment from about 0.75% to about 2% wt. %, based upon the total weight of the hydroalcoholic gel.

In one or more embodiments, the hydroalcoholic gel may further comprise a neutralizer. The use of neutralizing agents to form salts of carbomer polymers is known. Examples of neutralizing agents include amines, alkanolamines, alkanolamides, inorganic bases, amino acids, including salts, esters and acyl derivatives thereof.

Examples of common neutralizers are shown in Table 1, along with the manufacturers of these neutralizers, and the suggested ratio (per one part polymeric thickener) to achieve neutralization (pH 7.0) when the polymeric thickener has an equivalent weight of about 76+/−4.

TABLE 1

| Trade Name | CTFA Name | Manufacturer | Neutralization Ratio Base/ Carbopol ® Polymer |
|---|---|---|---|
| NaOH (18%) | Sodium Hydroxide | | 2.3/1.0 |
| Ammonia (28%) | Ammonium Hydroxide | | 0.7/1.0 |
| KOH (18%) | Potassium Hydroxide | | 2.7/1.0 |
| L-Arginine | Arginine | Ajinomoto | 4.5/1.0 |

TABLE 1-continued

| Trade Name | CTFA Name | Manufacturer | Neutralization Ratio Base/ Carbopol ® Polymer |
|---|---|---|---|
| AMP-95 ® | Aminomethyl Propanol | Angus | 0.9/1.0 |
| Neutrol ® TE | Tetrahydro-xypropyl Ethylenediamine | BASF | 2.3/1.0 |
| TEA (99%) | Triethanolamine | | 1.5/1.0 |
| Tris Amino ® (40%)* | Tromethamine | Angus | 3.3/1.0 |
| Ethomeen ® C-25 | PEG-15 Cocamine | Akzo | 6.2/1.0 |
| Diisopropanol-amine | Diisopropanol-amine | Dow | 1.2/1.0 |
| Triisopropanol-amine | Triisopropanol-amine | Dow | 1.5/1.0 |

In one or more embodiments, the neutralizer may be selected based on the amount of alcohol that is to be gelled. Table 2 shows commonly recommended neutralizers for hydroalcoholic systems.

TABLE 2

| Up to % Alcohol | Neutralizer |
|---|---|
| 20% | Sodium Hydroxide |
| 30% | Potassium Hydroxide |
| 60% | Triethanolamine |
| 60% | Tris Amino |
| 80% | AMP-95 ® |
| 90% | Neutrol TE |
| 90% | Diisopropanolamine |
| 90% | Triisopropanolamine |
| >90% | Ethomeen C-25 |

The hydroalcoholic gel further includes one or more plug-preventing additives. In general, the additive prevents the hydroalcoholic gel from coagulating into solid or semi-solid material that may deposit onto a surface or plug a dispenser nozzle. In one or more embodiments, the plug-preventing additive comprises a compound that includes from 2 to 6 ester groups or a polymeric ester that includes at least one ester group. In one embodiment, the plug-preventing additive comprises a monomeric or polymeric di-ester, tri-ester, tetra-ester, penta-ester, or hexa-ester, or a polymeric monoester.

In one or more embodiments, the plug-preventing additive includes one or more of C1-C30 alcohol esters of C1-C30 carboxylic acids, ethylene glycol monoesters of C1-C30 carboxylic acids, ethylene glycol diesters of C1-C30 carboxylic acids, propylene glycol monoesters of C1-C30 carboxylic acids, propylene glycol diesters of C1-C30 carboxylic acids, C1-C30 carboxylic acid monoesters and polyesters of polypropylene glycols, C1-C30 carboxylic acid monoesters and polyesters of polypropylene glycols, C1-C30 carboxylic acid monoesters and polyesters of C4-C20 alkyl ethers, C1-C30 carboxylic acid monoesters and polyesters of di-C8-C30 alkyl ethers, and mixtures thereof.

In one or more embodiments, the plug-preventing additive includes one or more of C1-C22 alcohol esters of C1-C22 carboxylic acids, C11-C22 alcohol esters of C3-C10 carboxylic acids, ethylene glycol monoesters of C1-C22 carboxylic acids, ethylene glycol diesters of C1-C22 carboxylic acids, propylene glycol monoesters of C1-C22 carboxylic acids, propylene glycol diesters of C1-C22 carboxylic acids, C1-C22 carboxylic acid monoesters and polyesters of polypropylene glycols, C1-C22 carboxylic acid monoesters and polyesters of polypropylene glycols, C1-C22 carboxylic acid monoesters and polyesters of C4-C22 alkyl ethers, C1-C22 carboxylic acid monoesters and polyesters of di-C8-C22 alkyl ethers, and mixtures thereof.

In one or more embodiments, the ester is formed from any of a variety of acids and alcohols. In one or more embodiments, at least one of the acid or alcohol includes a fatty chain. In one or more embodiments, the ester is formed from an acid having from about 4 to about 28 carbon atoms, and an alcohol having from about 2 to about 22 carbon atoms, in another embodiment, the ester is formed from an acid having from about 8 to about 22 carbon atoms, and an alcohol having from about 2 to about 22 carbon atoms.

Examples of ester plug-preventing additives include acetyl tributyl citrate, acetyl triethyl citrate, acetyl triethylhexyl citrate, acetyl trihexyl citrate, butyl benzyl phthalate, butyl phthalyl butyl glycolate, butyroyl trihexyl citrate, dibutyl adipate, dibutyloctyl malate, dibutyl oxalate, dibutyl phthalate, dibutyl sebacate, dicapryl adipate, dicaprylyl/capryl sebacate, diethylene glycol dibenzoate, diethylene glycol diethylhexanoate/diisononanoate, diethylene glycol diisononanoate, diethylene glycol rosinate, diethylhexyl adipate, diethylhexyl phthalate, diethylhexyl sebacate, diethylhexyl succinate, diethylhexyl terephthalate, diethyl oxalate, diethyl phthalate, diethyl sebacate, diethyl succinate, diisoamyl malate, diisobutyl adipate, diisobutyl maleate, diisobutyl oxalate, diisocetyl adipate, diisocetyl dodecanedioate, diisodecyl adipate, diisononyl adipate, diisocetyl adipate, diisooctyl maleate, diisooctyl sebacate, diisopropyl adipate, diisopropyl oxalate, diisopropyl sebacate, diisopropyl dimer dilinoleate, diisostearyl adipate, diisostearyl fumarate, diisostearyl glutarate, diisostearyl malate, diisostearyl sebacate, dimethyl adipate, dimethyl oxalate, dimethyl phthalate, dioctyldodecyl adipate, Dioctyldodecyl Dimer Dilinoleate, Dioctyldodecyl Dodecanedioate, Dioctyldodecyl Fluoroheptyl Citrate, Dioctyldodecyl IPDI, Dioctyldodecyl Lauroyl Glutamate, Dioctyldodecyl Malate, Dioctyldodecyl Sebacate, Dioctyldodecyl Stearoyl Glutamate, dipentaerythrityl hexa c5-9 acid esters, dipentaerythrityl hexa c5-10 acid esters, dipropyl oxalate, pentaerythrityl tetra c5-9 acid esters, pentaerythrityl tetra c5-10 acid esters, tributyl citrate, tricaprylyl/capryl trimellitate, triethyl citrate, triethylene glycol dibenzoate, triethylene glycol rosinate, triethylhexyl citrate, triethylhexyl trimellitate, trimethylpentanediyl dibenzoate, trimethyl pentanyl diisobutyrate, polyglyceryl-6 pentacaprylate, polyglyceryl-10 pentahydroxystearate, polyglyceryl-10 pentaisostearate, polyglyceryl-10 pentalaurate, polyglyceryl-10 pentalinoleate, polyglyceryl-5 pentamyristate, polyglyceryl-4 pentaoleate, polyglyceryl-6 pentaoleate, polyglyceryl-10 pentaoleate, polyglyceryl-3 pentaricinoleate, polyglyceryl-6 pentaricinoleate, polyglyceryl-10 pentaricinoleate, polyglyceryl-4 pentastearate, polyglyceryl-6 pentastearate, polyglyceryl-10 pentastearate, sorbeth-20 pentaisostearate, sorbeth-30 pentaisostearate, sorbeth-40 pentaisostearate, sorbeth-50 pentaisostearate, sorbeth-40 pentaoleate, sucrose pentaerucate, and triacetin, combinations thereof.

In one or more embodiments, the plug-preventing additive comprises a polymeric ester. In one embodiment, the polymeric ester includes a polyether polymer chain and at least one ester group. In one embodiment, the polymeric ester includes two or more ester groups.

In one or more embodiments, the polymer chain includes a polyethylene glycol (PEG) chain, a polypropylene glycol (PPG), or a combination thereof. In one or more embodiments, the polymer chain includes up to about 12 PEG units, PPG units, or a combination thereof. In one or more embodiments, the polymer chain includes up to about 10 PEG units, PPG units, or a combination thereof. In one or more embodiments, the polymer chain includes up to about 8 PEG units, PPG units, or a combination thereof. In one or more embodiments, the polyether polymer chain includes from about 1 to about 12 PPG or PEG units, in other embodiments from about 2 to about 8 PPG or PEG units, or a combination thereof.

Examples of polymeric esters include those that may be represented by the following formula

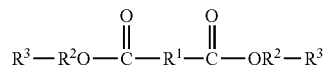

wherein $R^1$ is a linear or branched alkyl group having from 1 to 28 carbon atoms, each $R^2$, which may be the same or different, includes a polyether chain having from 1 to about 12 PEG or PPG groups, or a combination thereof, and each $R^3$, which may be the same or different, includes an alkyl or alkylene group having from 1 to about 30 carbon atoms, and wherein each $R^3$ group is attached to $R^2$ via an ether linkage.

In one or more embodiments, $R^1$ includes up to about 20 carbon atoms, in other embodiments, $R^1$ includes up to about 10 carbon atoms, and in other embodiments, $R^1$ includes up to about 8 carbon atoms. In one or more embodiments, $R^3$ may be represented by the formula $CH_3(CH_2)_zO-$, where in one or more embodiments z is an integer from 1 to about 21, in other embodiments from 2 to about 17, and in other embodiments from 3 to about 15.

In one or more embodiments, the polymeric ester may be represented by the following formula

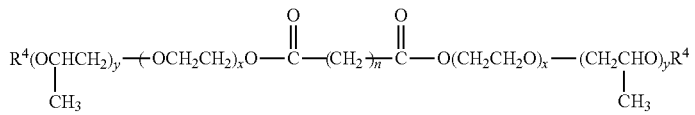

wherein $R^4$ includes a linear or branched, alkyl or alkylene group having from 1 to about 22 carbon atoms. In one or more embodiments, $R^4$ may be represented by the formula $CH_3(CH_2)_z-$, where in one or more embodiments z is an integer from 1 to about 21, in other embodiments from 2 to about 17, and in other embodiments from 3 to about 15. In one or more embodiments, n is an integer from 1 to about 20, in other embodiments from 2 to about 10. In one or more embodiments, x is zero, in other embodiments x is an integer up to about 12, in other embodiments up to about 10, in other embodiments up to about 8. In one or more embodiments, y is zero, in other embodiments, y is an integer up to about 12, in other embodiments up to about 10, and in other embodiments up to about 8.

Examples of polymeric esters further include those that may be represented by the following formula

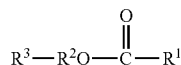

wherein $R^1$, $R^2$, and $R^3$ are as described hereinabove.

Examples of polymeric esters include any of the above di-, tri, tetra-, penta-, or hexa-esters modified to include a PPG, PEG, or PPG/PEG polymer chain of the appropriate length. Specific examples include Di-PPG-3-ceteth-4 adipate, Di-PPG-2-myreth-10 adipate, Di-PPG-3-myristyl ether adipate, and PPG-2 myristyl ether propionate. In one or more embodiments, a mixture of one or more polymeric esters and one or more monomeric di-, tri-, tetra-, penta-, or hexa-esters may be employed as plug-preventing additives.

In one embodiment, the plug-preventing additive is present in an amount of from about 0.005 to about 4 weight percent active, based upon the total weight of the hydroalcoholic gel composition. In another embodiment, the plug-preventing additive is present in an amount of from about 0.01 to about 1 weight percent, based upon the total weight of the hydroalcoholic gel composition, and in yet another embodiment, the plug-preventing additive is present in an amount of from about 0.02 to about 0.7 weight percent, based upon the total weight of the hydroalcoholic gel composition.

In one embodiment, the plug-preventing additive is added directly to the hydroalcoholic gel composition. In one or more other embodiments, the plug-preventing additive is added to the hydroalcoholic gel composition as a solution or emulsion. In other words, the plug-preventing additive may be premixed with a carrier to form a plug-preventing additive solution or emulsion, with the proviso that the carrier does not deleteriously affect the anti-clogging properties of the hydroalcoholic gel composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the plug-preventing additive is premixed to form a plug-preventing additive solution or emulsion, the amount of solution or emulsion that is added to the hydroalcoholic gel composition is selected so that the amount of plug-preventing additive falls within the ranges set forth hereinabove.

In one or more embodiments, the balance of the hydroalcoholic gel composition includes water or other suitable solvent. In one embodiment, one or more volatile silicone-based materials are included in the formulation to further aid the evaporation process. Exemplary volatile silicones have a lower heat of evaporation than alcohol. In certain embodiments, use of silicone-based materials can lower the surface tension of the fluid composition. This provides greater contact with the surface. In one embodiment, the silicone-based material, such as cyclomethicone, trimethylsiloxy silicate or a combination thereof, may be included in the formulation at a concentration of from about 4 wt. % to about 50 wt. % and in another embodiment from about 5 wt. % to about 35 wt. %, and in yet another embodiment from about 11 wt. % to about 25 wt. %, based upon the total weight of the hydroalcoholic gel composition.

The hydroalcoholic gel composition of this invention may further include a wide range of optional ingredients, with the proviso that they do not deleteriously affect the anti-clogging properties of the hydroalcoholic gel composition. The CTFA International Cosmetic Ingredient Dictionary and Handbook, Eleventh Edition, 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Non-limiting examples of functional classes of ingredients are described in these references. Examples of these functional classes include: abrasives, anti-acne agents, anticaking agents, antioxidants, binders, biological additives, botanicals, bulking agents, chelating agents, chemical additives; colorants, cosmetic astringents, cosmetic biocides, denaturants, drug astringents, emulsifiers, external analgesics, film formers, fragrance components, humectants, odor-neutralizing agents, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, and keratolytics, and the like. In one or more embodiments, one or more ingredients may be encapsulated or microencapsulated. For example, actives, colorants, fragrances, flavors, botanicals, solids, or other synthetic components may be present in the composition in encapsulated form.

Surfactants may be included in the hydroalcoholic gel compositions for the purpose of boosting or modifying the gel quality and characteristics, for modifying the feel of the final formulation during rub in and/or dry time, for providing persistence or long-lasting microbial action of the alcohol, for solubilizing other ingredients such as fragrances or sunscreens, and for irritation mitigation. Optional surfactants include, but are not necessarily limited to, sulfosuccinates, amine oxides, PEG-80 sorbitan laurate, polyglucosides, alkanolamides, sorbitan derivatives, fatty alcohol ethoxylates, quaternary ammonium compounds, amidoamines, sultaines, isothionates, sarcosinates, betaines, polysorbates and fatty alcohol polyethylene glycols.

In one or more embodiments, the hydroalcoholic gel composition comprises one or more of the following optional components: glycerin, fragrance, isopropyl myristate, titanium dioxide, alumina, tocopheryl acetate, aloe extract, dye, and propylene glycol. In these or other embodiments, the hydroalcoholic gel composition includes one or more auxiliary thickeners, such as cationic polymeric thickeners.

The amount of optional components is not particularly limited, so long as the optional components do not deleteriously affect the anti-clogging properties of the hydroalcoholic gel composition. In certain embodiments, one or more auxiliary agents may be present in the hydroalcoholic gel composition in an amount of from about 0 to about 2 weight percent, based upon the total weight of the hydroalcoholic gel composition. In other embodiments, one or more auxiliary agents may be present in the hydroalcoholic gel composition in an amount of from about 0.1 to about 1 weight percent, based upon the total weight of the hydroalcoholic gel composition.

In certain embodiments, the hydroalcoholic gel composition comprises one or more humectants. Examples of humectants include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like. In one embodiment, the humectant is present in an amount of from about 0.1 to about 20% by weight, based upon the total weight of the hydroalcoholic gel composition. In another embodiment the humectant is present in an amount of from about 1 to about 8% by weight, in another embodiment from about 2 to about 3% by weight, based upon the total weight of the hydroalcoholic gel composition.

In these or other embodiments, the hydroalcoholic gel composition comprises one or more conditioning or moisturizing esters. Examples of esters include cetyl myristate, cetyl myristoleate, and other cetyl esters, and isopropyl myristate. In one embodiment, the ester is present in an amount of up to 10% by weight, based upon the total weight of the hydroalcoholic gel composition. In another embodiment the ester is present in an amount of from about 0.5 to about 5% by weight, in another embodiment from about 1 to about 2% by weight, based upon the total weight of the hydroalcoholic gel composition.

In one or more embodiments, the hydroalcoholic gel composition includes one or more emulsifying agents. Examples of emulsifying agents include stearyl alcohol, sorbitan oleate trideceth-2, poloxamers, and PEG/PPG-20/6 dimethicone. In one embodiment, the emulsifying agent is present in an amount of up to about 10% by weight, based upon the total weight of the hydroalcoholic gel composition. In another embodiment the emulsifying agent is present in an amount of from about 0.1 to about 5% by weight, in another embodiment from about 0.5 to about 2% by weight, based upon the total weight of the hydroalcoholic gel composition.

In one or more embodiments, the hydroalcoholic gel composition includes one or more solubilizers. Examples of solubilizers include PEG-40 hydrogenated castor oil, polysorbate-80, PEG-80 sorbitan laurate, ceteareth-20, oleth-20, PEG-4, and propylene glycol. The amount of solubilizer is not particularly limited, so long as it does not deleteriously affect the anti-clogging properties of the hydroalcoholic gel composition.

In one embodiment, alcohol is the only active antimicrobial ingredient introduced into the composition. In this embodiment, the amount of auxiliary antimicrobial ingredients is less than about 0.5 wt. %, and in another embodiment, less than about 0.1 wt. %, based upon the total weight of the hydroalcoholic gel composition. In other embodiments, the composition includes auxiliary antimicrobial agents in addition to alcohol.

The hydroalcoholic gel composition of the present invention may optionally further comprise a wide range of topical drug actives, with the proviso that they do not deleteriously affect the anti-clogging properties of the hydroalcoholic gel composition.

For reasons including solubility and aesthetics, one or more of any of the optional ingredients listed above may be limited. In one or more embodiments, the amount of the limited optional ingredient is less than about 0.5 percent by weight, in another embodiment, less than about 0.1 percent by weight, based upon the total weight of the hydroalcoholic gel composition. In another embodiment, the hydroalcoholic gel composition is devoid of the limited optional ingredient.

For reasons including solubility and aesthetics, one or more of the following components may be limited. In one or more embodiments, the amount of fatty alcohol is limited. In one embodiment, the amount of fatty alcohol is less than about 0.5 percent by weight, in another embodiment, less than about 0.1 percent by weight, based upon the total weight of the hydroalcoholic gel composition. In another embodiment, the hydroalcoholic gel composition is devoid of fatty alcohol.

In one or more embodiments, the amount of petrolatum or mineral oil is limited. In one embodiment, the amount of petrolatum or mineral oil is less than about 0.5 percent by weight, in another embodiment, less than about 0.1 percent by weight, based upon the total weight of the hydroalcoholic gel composition. In another embodiment, the hydroalcoholic gel composition is devoid of petrolatum or mineral oil. In these or other embodiments, the total amount of fatty alcohol, petrolatum, and mineral oil is less than about 1 wt. %.

In one or more embodiments, the amount of glycerin is limited. In one embodiment, the amount of glycerin is less than about 1 percent by weight, in another embodiment, less than about 0.5 percent by weight, based upon the total weight of the hydroalcoholic gel composition. In another embodiment, the hydroalcoholic gel composition is devoid of glycerin.

The dispensable hydroalcoholic gel composition may be prepared by simply mixing the components together. The order of addition is not particularly limited. In one embodiment, the hydroalcoholic gel composition is prepared by a method comprising dispersing the polymeric thickener in alcohol with slow to moderate agitation, adding water, and then adding a plug-preventing additive, and mixing until the mixture is homogeneous. In other embodiments, the hydroalcoholic gel composition is prepared by a method comprising dispersing the polymeric thickener in water with slow to moderate agitation, adding alcohol, a plug-preventing additive, and mixing until the mixture is homogeneous. In one or more embodiments, a neutralizer is added to the mixture to neutralize the thickener and form the gel. Those of skill in the art will understand that optional ingredients may be added at various points during the mixing process. It will also be understood that a gel may be formed without a neutralizer if the thickener is one that swells when mixed with water or alcohol.

The hydroalcoholic gel composition of the present invention may be employed in any type of dispenser typically used for gel products, for example pump dispensers. A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT® and TFX™ as well as traditional bag-in-box dispensers. Examples of dispensers are described in U.S. Pat. Nos. 5,265,772, 5,944,227, 6,877,642, 7,028,861, and U.S. Published Application Nos. 2006/0243740 A1 and 2006/0124662 A1, all of which are incorporated herein by reference. In one or more embodiments, the dispenser includes an outlet such as a nozzle, through which the hydroalcoholic gel composition is dispensed.

In one or more embodiments, the hydroalcoholic gel of the present invention exhibited less misdirection upon being dispensed than did common hydroalcoholic gels that did not contain an anti-plug agent. Frequency of mis-directed output may be determined as a percentage of total dispenser actuations. Comparative measurements may be taken at various rates of actuation. An output target may be created to distinguish between acceptable output and mis-directed output. In one or more embodiments, the output target simulates the hand(s) of the dispenser user. The output target defines a zone of acceptable output. In one or more embodiments, when an effective amount of an anti-plug agent is added to a hydroalcoholic gel composition, the frequency of mis-directed output may be reduced. In certain embodiments, the dispenser output will be outside of a 2.5 inch square zone about 3 inches directly below the dispenser nozzle with less than 50% frequency when the rate of dispenser actuation is 0.1 actuations per hour. In other embodiments, the dispenser output will be outside of a 2.5 inch square zone about 3 inches directly below the dispenser nozzle with less than 30% frequency when the rate of dispenser actuation is 0.1 actuations per hour. In one or more embodiments, the dispenser output will be outside of a 2.5 inch square zone about 3 inches directly below the dispenser nozzle with less than 20% frequency when the rate of dispenser actuation is 0.1 actuations per hour. In one embodiment, the dispenser output will be outside of a 2.5 inch square zone about 3 inches directly below the dispenser nozzle with less than 15% frequency when the rate of dispenser actuation is 0.1 actuations per hour. In one or more embodiments, substantially none of the dispenser output will be outside of a 2.5 inch square zone about 3 inches directly below the dispenser nozzle when the rate of dispenser actuation is 0.1 actuations per hour.

In one or more embodiments, when an effective amount of an anti-plug agent is added to a hydroalcoholic gel composition, the frequency of mis-directed output may be reduced. In certain embodiments, the dispenser output will be outside of a 2.5 inch square zone about 3 inches directly below the dispenser nozzle with less than 10% frequency when the rate of dispenser actuation is 0.1 actuations per hour. In other embodiments, the dispenser output will be outside of a 2.5 inch square zone about 3 inches directly below the dispenser nozzle with less than 5% frequency when the rate of dispenser actuation is 0.1 actuations per hour. In one or more embodiments, the dispenser output will be outside of a 2.5 inch square zone about 3 inches directly below the dispenser nozzle with less than 1% frequency when the rate of dispenser actuation is 0.1 actuations per hour. In one embodiment, the dispenser output will be outside of a 2.5 inch square zone about 3 inches directly below the dispenser nozzle with less than 0.5% frequency when the rate of dispenser actuation is 0.1 actuations per hour. In one or more embodiments, substantially none of the dispenser output will be outside of a 2.5 inch square zone about 3 inches directly below the dispenser nozzle when the rate of dispenser actuation is 0.1 actuations per hour.

In certain embodiments, the dispenser output will be outside of a 2.5 inch square zone about 3 inches directly below the dispenser nozzle with less than 40% frequency when the rate of dispenser actuation is 0.5 actuations per hour. In other embodiments, the dispenser output will be outside of a 2.5 inch square zone about 3 inches directly below the dispenser nozzle with less than 30% frequency when the rate of dispenser actuation is 0.5 actuations per hour. In one or more embodiments, the dispenser output will be outside of a 2.5 inch square zone about 3 inches directly below the dispenser nozzle with less than 20% frequency when the rate of dispenser actuation is 0.5 actuations per hour. In one embodiment, the dispenser output will be outside of a 2.5 inch square zone about 3 inches directly below the dispenser nozzle with less than 15% frequency when the rate of dispenser actuation is 0.5 actuations per hour. In one or more embodiments, substantially none of the dispenser output will be outside of a 2.5 inch square zone about 3 inches directly below the dispenser nozzle when the rate of dispenser actuation is 0.5 actuations per hour.

In certain embodiments, the dispenser output will be outside of a 2.5 inch square zone about 3 inches directly below the dispenser nozzle with less than 10% frequency when the rate of dispenser actuation is 0.5 actuations per hour. In other embodiments, the dispenser output will be outside of a 2.5 inch square zone about 3 inches directly below the dispenser nozzle with less than 5% frequency when the rate of dispenser actuation is 0.5 actuations per hour. In one or more embodiments, the dispenser output will be outside of a 2.5 inch square zone about 3 inches directly below the dispenser nozzle with less than 1% frequency when the rate of dispenser actuation is 0.5 actuations per hour. In one embodiment, the dispenser output will be outside of a 2.5 inch square zone about 3 inches directly below the dispenser nozzle with less than 0.5% frequency when the rate of dispenser actuation is 0.5 actuations per hour. In one or more embodiments, substantially none of the dispenser output will be outside of a 2.5 inch square zone about 3 inches directly below the dispenser nozzle when the rate of dispenser actuation is 0.5 actuations per hour.

In certain embodiments, the dispenser output will be outside of a 2.5 inch square zone about 3 inches directly below the dispenser nozzle with less than 40% frequency when the rate of dispenser actuation is 3 actuations per hour. In other embodiments, the dispenser output will be outside of a 2.5 inch square zone about 3 inches directly below the dispenser nozzle with less than 30% frequency when the rate of dispenser actuation is 3 actuations per hour. In one or more embodiments, the dispenser output will be outside of a 2.5 inch square zone about 3 inches directly below the dispenser nozzle with less than 20% frequency when the rate of dispenser actuation is 3 actuations per hour. In one embodiment, the dispenser output will be outside of a 2.5 inch square zone about 3 inches directly below the dispenser nozzle with less than 15% frequency when the rate of dispenser actuation is 3 actuations per hour. In one or more embodiments, substantially none of the dispenser output will be outside of a 2.5 inch square zone about 3 inches directly below the dispenser nozzle when the rate of dispenser actuation is 3 actuations per hour.

In certain embodiments, the dispenser output will be outside of a 2.5 inch square zone about 3 inches directly below the dispenser nozzle with less than 10% frequency when the rate of dispenser actuation is 3 actuations per hour. In other embodiments, the dispenser output will be outside of a 2.5 inch square zone about 3 inches directly below the dispenser nozzle with less than 5% frequency when the rate of dispenser actuation is 3 actuations per hour. In one or more embodiments, the dispenser output will be outside of a 2.5 inch square zone about 3 inches directly below the dispenser nozzle with less than 1% frequency when the rate of dispenser actuation is 3 actuations per hour. In one embodiment, the dispenser output will be outside of a 2.5 inch square zone about 3 inches directly below the dispenser nozzle with less than 0.5% frequency when the rate of dispenser actuation is 3 actuations per hour. In one or more embodiments, substantially none of the dispenser output will be outside of a 2.5 inch square zone about 3 inches directly below the dispenser nozzle when the rate of dispenser actuation is 3 actuations per hour.

In one or more embodiments, the effectiveness of the plug-preventing additive may be expressed in terms of the percent reduction in the frequency of misdirection. That is, a hydroalcoholic gel composition containing a plug-preventing additive may be tested in comparison to a control that does not contain a plug-preventing additive. The frequency of misdirection may be determined as described hereinabove, and the percent reduction in frequency of misdirection may be calculated for the composition containing the plug-preventing additive compared to the control. More generally, the percent reduction in the frequency of misdirection may be calculated for any rate of actuation and any output target zone relative to a control composition that does not contain any plug-preventing additive and is tested under the same conditions. In one or more embodiments, the percent reduction in the frequency of misdirection is at least about 50%. In other embodiments, the percent reduction in the frequency of misdirection is at least about 60%, in yet other embodiments, at least about 70% in still other embodiments, at least about 80%. In one or more embodiments, the percent reduction in the frequency of misdirection is at least about 90%, in other embodiments, at least about 95%, and in yet other embodiments, at least about 97%.

In order to demonstrate the practice of the present invention, the following examples have been prepared and tested. The examples should not, however, be viewed as limiting the scope of the invention. The claims will serve to define the invention.

EXAMPLES

Examples 1-7

Hydroalcoholic gel formulations were prepared by mixing ingredients in the amounts shown in the following tables 3 to 6. The gels were dispensed by using a GOJO NXT® side-by-side dispenser with 1000 ml refills and DP1 pumps. The dispenser is ADA compliant, and features one-hand push operation. The rate of actuations was held constant for all samples. The output target was positioned about 3 inches below the nozzle tip, and was defined by a 2.5 inch square. The percentage of mis-direction based upon the total number of actuations is provided for each composition.

The tests were performed over 15 days, and each sample was tested in multiple dispensers. Thus, the percentage data in the tables below is the average of up to about 900 actuations that were observed for each formulation. Where the frequency of mis-direction was relatively high, deposits of coagulated gel were observed on surfaces of the dispenser nozzle.

TABLE 3

| Weight % | Example 1 | Example 2 | Example 3 |
| --- | --- | --- | --- |
| Water | qs | qs | qs |
| Acrylates/C 10-30 AlkylAcrylate | 0.3 | 0.3 | 0.3 |
| Ethanol SDA 3C | 74 | 74 | 74 |
| Glycerin | 0.25 | 0.25 | 0.25 |
| Aminomethyl Propanol (95%) | .098 | .098 | 0.098 |
| Diisopropyl Sebacate | 0.25 | — | 0.25 |
| PEG/PPG-20/6 dimethicone (65%) | 0.10 | — | — |
| Fragrance | — | — | 0.13 |
| Tocopheryl Acetate | — | — | 0.001 |
| Isopropyl Myristate | 0.25 | 0.001 | 0.001 |
| % Misdirection | 2.0 | 52.0 | 7.7 |

TABLE 4

| Weight % | Example 4 | Example 5 |
| --- | --- | --- |
| Water | qs | qs |
| Carbomer | 0.25 | 0.25 |
| Ethanol SDA 3C | 65 | 65 |
| Glycerin | 0.25 | 0.25 |
| Aminomethyl Propanol | 0.098 | 0.098 |
| Diisopropyl Sebacate | — | 0.5 |
| Isopropyl Myristate | 0.5 | — |
| % Misdirection | 7.1 | 0 |

TABLE 5

| Weight % | Example 6 |
| --- | --- |
| Water | qs |
| Carbomer | 0.23 |
| Ethanol SDA 3C | 64.5 |
| Glycerin | 0.25 |
| Aminomethyl Propanol | 0.098 |
| Diisopropyl Sebacate | — |
| Isopropyl Myristate | 0.001 |
| Fragrance | 0.13 |
| Tocopheryl Acetate | 0.001 |
| % Misdirection | 35.0 |

TABLE 6

| Weight % | Example 7 |
| --- | --- |
| Water | qs |
| Carbomer | 0.23 |
| Ethanol SDA 3C | 64.5 |
| Glycerin | 0.25 |
| Aminomethyl Propanol | 0.098 |
| Diisopropyl Sebacate | 0.25 |
| Isopropyl Myristate | — |
| Fragrance | 0.13 |
| Tocopheryl Acetate | 0.0001 |
| % Misdirection | 0.44 |

Examples 8-16

Examples 8-16 are hydroalcoholic gel formulations that contain about 74 wt. % ethanol SDA 3 C. They also each contain the same amount of the following ingredients: Acrylates/C10-30 alkyl acrylate crosspolymer, glycerin, aminomethyl propanol, and water. Examples 8-16 differ in the amount and type of plug-preventing additive that was included in the formulation. These are summarized below in Table 7. Example 9 differs from Example 8 only in that Example 9 includes 0.13 wt. % fragrance. Examples 8-16 were dispensed and tested for frequency of mis-direction as described above for Examples 1-7. Example 8 was designated as a control, against which the frequency of mis-direction was normalized for Examples 9-16. Table 7 summarizes the percent reduction in the frequency of misdirection, which may also be referred to as the percent reduction in mis-directed output, for Examples 9-16 relative to Example 8.

TABLE 7

| Example No. | Plug-Preventing Additive (wt. %) | (%) Reduction Mis-directed Output |
| --- | --- | --- |
| 8 | None | N/A |
| 9 | None | 5.66 |
| 10 | 0.25% Di-PPG-3-ceteth-4 adipate | 97.13 |
| 11 | 0.5% Di-PPG-3-ceteth-4 adipate | 98.19 |
| 12 | 0.5% Di-PPG-2-myreth-10 adipate | 97.94 |
| 13 | 0.5% Di-PPG-3 myristyl ether adipate | 98.45 |

TABLE 7-continued

| Example No. | Plug-Preventing Additive (wt. %) | (%) Reduction Mis-directed Output |
|---|---|---|
| 14 | 0.5% PPG-2 myristyl ether propionate | 99.37 |
| 15 | 0.5% triacetin | 55.75 |
| 16 | 1.0% triacetin | 57.95 |

Various modifications and alterations that do not depart from the scope and spirit of this invention will become apparent to those skilled in the art. This invention is not to be duly limited to the illustrative embodiments set forth herein.

What is claimed is:

1. A method of reducing the formation of coagulated gel deposits, the method comprising the steps of:
combining a $C_{1-4}$ alcohol, an effective amount of a polyacrylate thickener; and a plug-preventing additive to form a dispensable gel composition having a viscosity of from about 5,000 to about 35,000 cps, when measured using RV or LV spindles at about 22° C.; wherein said plug-preventing additive comprises an ester having from two to six ester groups or a polymeric ester that includes at least one ester group; and wherein said composition comprises at least about 40 wt. % of said alcohol, wherein the composition is devoid of fatty alcohol, and wherein the composition is devoid of petrolatum, mineral oil, or mixtures thereof, all based upon the total weight of the dispensable gel composition; and storing the dispensable gel in a pump-type dispenser that is activated on a periodic basis, wherein the formation of coagulated gel deposits is reduced when compared to a dispensable gel that does not include the plug-preventing additive.

2. The method of claim 1, wherein said alcohol comprises methanol, ethanol, propanol, isopropanol, butanol, isobutanol, tertiary butanol, or mixtures thereof.

3. The method of claim 1, wherein said ester plug-preventing additive comprises one or more of C1-C30 alcohol esters of C1-C30 carboxylic acids, ethylene glycol monoesters of C1-C30 carboxylic acids, ethylene glycol diesters of C1-C30 carboxylic acids, propylene glycol monoesters of C1-C30 carboxylic acids, propylene glycol diesters of C1-C30 carboxylic acids, C1-C30 carboxylic acid monoesters and polyesters of polypropylene glycols, C1-C30 carboxylic acid monoesters and polyesters of polypropylene glycols, C1-C30 carboxylic acid monoesters and polyesters of C4-C20 alkyl ethers, C1-C30 carboxylic acid monoesters and polyesters of di-C8-C30 alkyl ethers, and mixtures thereof.

4. The method of claim 1, wherein said ester plug-preventing additive comprises one or more of C1-C22 alcohol esters of C1-C22 carboxylic acids, C11-C22 alcohol esters of C3-C10 carboxylic acids, ethylene glycol monoesters of C1-C22 carboxylic acids, ethylene glycol diesters of C1-C22 carboxylic acids, propylene glycol monoesters of C1-C22 carboxylic acids, propylene glycol diesters of C1-C22 carboxylic acids, C1-C22 carboxylic acid monoesters and polyesters of polypropylene glycols, $C_1$-$C_{22}$ carboxylic acid monoesters and polyesters of polypropylene glycols, C1-C22 carboxylic acid monoesters and polyesters of C4-C22 alkyl ethers, $C_1$-C22 carboxylic acid monoesters and polyesters of di-C8-C22 alkyl ethers, and mixtures thereof.

5. The method of claim 1, wherein said ester plug-preventing additive is formed from an acid having from about 4 to about 28 carbon atoms, and an alcohol having from about 2 to about 22 carbon atoms.

6. The method of claim 1, wherein said ester plug-preventing additive comprises a polymer chain that includes up to about 12 PEG units, PPG units, or a combination thereof.

7. The method of claim 1, wherein said ester plug-preventing additive is represented by the formula

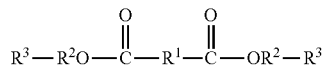

wherein $R^1$ is a linear or branched alkyl group, having from 1 to about 28 carbon atoms, wherein each $R^2$, which may be the same or different, includes a polyether chain having from 1 to about 12 PEG or PPG groups, or a combination thereof, wherein each $R^3$, which may be the same or different, includes a linear or branched alkyl or alkylene group having from 1 to about 30 carbon atoms, and wherein each $R^3$ group is attached to $R^2$ via an ether linkage.

8. The method of claim 1, wherein said ester plug-preventing additive is represented by the formula

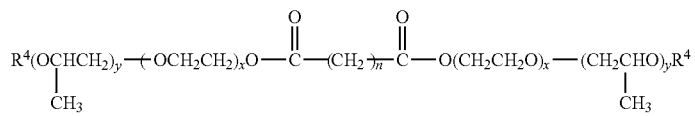

wherein $R^4$ includes a linear or branched, alkyl or alkylene group having from 1 to about 22 carbon atoms, wherein n is an integer from 1 to about 20, wherein x is zero or an integer up to about 12, and wherein y is zero or an integer up to about 12.

9. The method of claim 1, wherein said ester plug-preventing additive is represented by the formula

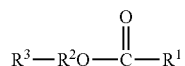

wherein $R^1$ is a linear or branched alkyl group, having from 1 to about 28 carbon atoms, wherein $R^2$ includes a polyether chain having from 1 to about 12 PEG or PPG groups, or a combination thereof, wherein $R^3$ includes a linear or branched alkyl or alkylene group having from 1 to about 30 carbon atoms, and wherein $R^3$ is attached to $R^2$ via an ether linkage.

10. The method of claim 1, wherein said ester plug-preventing additive comprises acetyl tributyl citrate, acetyl triethyl citrate, acetyl triethylhexyl citrate, acetyl trihexyl citrate, butyl benzyl phthalate, butyl phthalyl butyl glycolate, butyroyl trihexyl citrate, dibutyl adipate, dibutyloctyl malate, dibutyl oxalate, dibutyl phthalate, dibutyl sebacate, dicapryl adipate, dicaprylyl/capryl sebacate, diethylene glycol dibenzoate, diethylene glycol diethylhexanoate/diisononanoate, diethylene glycol diisononanoate, diethylene glycol rosinate, diethylhexyl adipate, diethylhexyl phthalate, diethylhexyl sebacate, diethylhexyl succinate, diethylhexyl terephthalate, diethyl oxalate, diethyl phthalate, diethyl sebacate, diethyl succinate, diisoamyl malate, diisobutyl adipate, diisobutyl maleate, diisobutyl oxalate, diisocetyl adipate, diisocetyl dodecanedioate, diisodecyl adipate, diisononyl adipate, diisocetyl adipate, diisooctyl maleate, diisooctyl sebacate, diisopropyl adipate, diisopropyl oxalate, diisopropyl sebacate, diisopropyl dimer dilinoleate, diisostearyl adipate, diisostearyl fumarate, diisostearyl glutarate, diisostearyl malate, diisostearyl sebacate, dimethyl adipate, dimethyl oxalate, dimethyl phthalate, dioctyldodecyl adipate, Dioctyldodecyl Dimer Dilinoleate, Dioctyldodecyl Dodecanedioate, Dioctyldodecyl Fluoroheptyl Citrate, Dioctyldodecyl IPDI, Dioctyldodecyl Lauroyl Glutamate, Dioctyldodecyl Malate, Dioctyldodecyl Sebacate, Dioctyldodecyl Stearoyl Glutamate, dipentaerythrityl hexa c5-9 acid esters, dipentaerythrityl hexa c5-10 acid esters, dipropyl oxalate, pentaerythrityl tetra c5-9 acid esters, pentaerythrityl tetra c5-10 acid esters, tributyl citrate, tricaprylyl/capryl trimellitate, triethyl citrate, triethylene glycol dibenzoate, triethylene glycol rosinate, triethylhexyl citrate, triethylhexyl trimellitate, trimethylpentanediyl dibenzoate, trimethyl pentanyl diisobutyrate, polyglyceryl-6 pentacaprylate, polyglyceryl-10 pentahydroxystearate, polyglyceryl-10 pentaisostearate, polyglyceryl-10 pentalaurate, polyglyceryl-10 pentalinoleate, polyglyceryl-5 pentamyristate, polyglyceryl-4 pentaoleate, polyglyceryl-6 pentaoleate, polyglyceryl-10 pentaoleate, polyglyceryl-3 pentaricinoleate, polyglyceryl-6 pentaricinoleate, polyglyceryl-10 pentaricinoleate, polyglyceryl-4 pentastearate, polyglyceryl-6 pentastearate, polyglyceryl-10 pentastearate, sorbeth-20 pentaisostearate, sorbeth-30 pentaisostearate, sorbeth-40 pentaisostearate, sorbeth-50 pentaisostearate, sorbeth-40 pentaoleate, sucrose pentaerucate, triacetin, Di-PPG-3-ceteth-4 adipate, Di-PPG-2-myreth-10 adipate, Di-PPG-3-Myristyl ether adipate, PPG-2 Myristyl ether propionate, or a mixture thereof.

11. The method of claim 1, wherein said ester plug-preventing additive comprises Di-PPG-3-ceteth-4 adipate, Di-PPG-2-myreth-10 adipate, Di-PPG-3-myristyl ether adipate, PPG-2 myristyl ether propionate, or a mixture thereof.

12. The method of claim 1, wherein said polyacrylate thickener is selected from the group consisting of carbomers, acrylates/C 10-30 alkyl acrylate crosspolymers, copolymers of acrylic acid and alkyl (C5-C10) acrylate, copolymers of acrylic acid and maleic anhydride, and mixtures thereof.

13. The method of claim 1, wherein the composition comprises from about 0.005 to about 4 wt. % ester plug-preventing additive, based upon the total weight of the composition.

14. A method of reducing the frequency of mis-directed output from a gel dispenser, the method comprising the steps of:

combining a $C_{1-4}$ alcohol, an effective amount of a polyacrylate thickener; and a plug-preventing additive to form a dispensable gel composition having a viscosity of from about 5,000 to about 35,000 cps, when measured using RV or LV spindles at about 22° C.; wherein said plug-preventing additive comprises an ester having from two to six ester groups or a polymeric ester that includes at least one ester group; and wherein said composition comprises at least about 40 wt. % of said alcohol, wherein the composition is devoid of fatty alcohol, and wherein the composition is devoid of petrolatum, mineral oil, or mixtures thereof, all based upon the total weight of the dispensable gel composition; and storing the dispensable gel in a pump-type dispenser that includes an outlet and that is activated on a periodic basis, wherein the frequency of mis-directed output is reduced when compared to a dispensable gel that does not include the plug-preventing additive.

15. The method of claim 14, wherein the dispenser output will be outside of a 2.5 inch square zone about 3 inches directly below the dispenser outlet with less than 50% frequency when the rate of dispenser actuation is 0.1 actuations per hour.

16. The method of claim 14, wherein the reduction in the frequency of mis-directed dispenser output is at least about 50%, when compared to a control gel that is tested under the same conditions.

17. The method of claim 14, wherein the reduction in the frequency of mis-directed dispenser output is at least about 70%, when compared to a control gel that is tested under the same conditions.

18. The method of claim 14, wherein the reduction in the frequency of mis-directed dispenser output is at least about 90%, when compared to a control gel that is tested under the same conditions.

19. The method of claim 14, wherein said ester plug-preventing additive comprises a polymer chain that includes up to about 12 PEG units, PPG units, or a combination thereof.

20. The method of claim 14, wherein said ester plug-preventing additive is represented by the formula

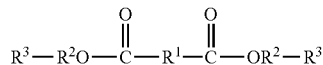

wherein $R^1$ is a linear or branched alkyl group, having from 1 to about 28 carbon atoms, wherein each $R^2$, which may be the same or different, includes a polyether chain having from 1 to about 12 PEG or PPG groups, or a combination thereof, wherein each $R^3$, which may be the same or different, includes a linear or branched alkyl or alkylene group having from 1 to about 30 carbon atoms, and wherein each $R^3$ group is attached to $R^2$ via an ether linkage.

21. The method of claim 14, wherein said ester plug-preventing additive is represented by the formula

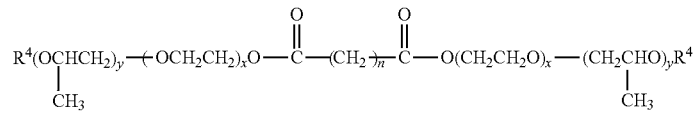

wherein $R^4$ includes a linear or branched, alkyl or alkylene group having from 1 to about 22 carbon atoms, wherein n is an integer from 1 to about 20, wherein x is zero or an integer up to about 12, and wherein y is zero or an integer up to about 12.

22. The method of claim 14, wherein said ester plug-preventing additive is represented by the formula

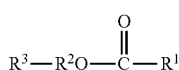

wherein $R^1$ is a linear or branched alkyl group, having from 1 to about 28 carbon atoms, wherein $R^2$ includes a polyether chain having from 1 to about 12 PEG or PPG groups, or a combination thereof, wherein $R^3$ includes a linear or branched alkyl or alkylene group having from 1 to about 30 carbon atoms, and wherein $R^3$ is attached to $R^2$ via an ether linkage.

23. The method of claim 14, wherein said ester plug-preventing additive comprises acetyl tributyl citrate, acetyl triethyl citrate, acetyl triethylhexyl citrate, acetyl trihexyl citrate, butyl benzyl phthalate, butyl phthalyl butyl glycolate, butyroyl trihexyl citrate, dibutyl adipate, dibutyloctyl malate, dibutyl oxalate, dibutyl phthalate, dibutyl sebacate, dicapryl adipate, dicaprylyl/capryl sebacate, diethylene glycol dibenzoate, diethylene glycol diethylhexanoate/diisononanoate, diethylene glycol diisononanoate, diethylene glycol rosinate, diethylhexyl adipate, diethylhexyl phthalate, diethylhexyl sebacate, diethylhexyl succinate, diethylhexyl terephthalate, diethyl oxalate, diethyl phthalate, diethyl sebacate, diethyl succinate, diisoamyl malate, diisobutyl adipate, diisobutyl maleate, diisobutyl oxalate, diisocetyl adipate, diisocetyl dodecanedioate, diisodecyl adipate, diisononyl adipate, diisocetyl adipate, diisooctyl maleate, diisooctyl sebacate, diisopropyl adipate, diisopropyl oxalate, diisopropyl sebacate, diisopropyl dimer dilinoleate, diisostearyl adipate, diisostearyl fumarate, diisostearyl glutarate, diisostearyl malate, diisostearyl sebacate, dimethyl adipate, dimethyl oxalate, dimethyl phthalate, dioctyldodecyl adipate, Dioctyldodecyl Dimer Dilinoleate, Dioctyldodecyl Dodecanedioate, Dioctyldodecyl Fluoroheptyl Citrate, Dioctyldodecyl IPDI, Dioctyldodecyl Lauroyl Glutamate, Dioctyldodecyl Malate, Dioctyldodecyl Sebacate, Dioctyldodecyl Stearoyl Glutamate, dipentaerythrityl hexa c5-9 acid esters, dipentaerythrityl hexa c5-10 acid esters, dipropyl oxalate, pentaerythrityl tetra c5-9 acid esters, pentaerythrityl tetra c5-10 acid esters, tributyl citrate, tricaprylyl/capryl trimellitate, triethyl citrate, triethylene glycol dibenzoate, triethylene glycol rosinate, triethylhexyl citrate, triethylhexyl trimellitate, trimethylpentanediyl dibenzoate, trimethyl pentanyl diisobutyrate, polyglyceryl-6 pentacaprylate, polyglyceryl-10 pentahydroxystearate, polyglyceryl-10 pentaisostearate, polyglyceryl-10 pentalaurate, polyglyceryl-10 pentalinoleate, polyglyceryl-5 pentamyristate, polyglyceryl-4 pentaoleate, polyglyceryl-6 pentaoleate, polyglyceryl-10 pentaoleate, polyglyceryl-3 pentaricinoleate, polyglyceryl-6 pentaricinoleate, polyglyceryl-10 pentaricinoleate, polyglyceryl-4 pentastearate, polyglyceryl-6 pentastearate, polyglyceryl-10 pentastearate, sorbeth-20 pentaisostearate, sorbeth-30 pentaisostearate, sorbeth-40 pentaisostearate, sorbeth-50 pentaisostearate, sorbeth-40 pentaoleate, sucrose pentaerucate, triacetin, Di-PPG-3-ceteth-4 adipate, Di-PPG-2-myreth-10 adipate, Di-PPG-3-Myristyl ether adipate, PPG-2 Myristyl ether propionate, or a mixture thereof.

24. The method of claim 14, wherein said ester plug-preventing additive comprises Di-PPG-3-ceteth-4 adipate, Di-PPG-2-myreth-10 adipate, Di-PPG-3-myristyl ether adipate, PPG-2 myristyl ether propionate, or a mixture thereof.

25. The method of claim 14, wherein said polyacrylate thickener is selected from the group consisting of carbomers, acrylates/C 10-30 alkyl acrylate crosspolymers, copolymers of acrylic acid and alkyl (C5-C10) acrylate, copolymers of acrylic acid and maleic anhydride, and mixtures thereof.

26. The method of claim 14, wherein the composition comprises from about 0.005 to about 4 wt. % ester plug-preventing additive, based upon the total weight of the composition.

27. The method of claim 14, wherein the composition is devoid of topical drug actives.

28. The method of claim 14, wherein the composition comprises less than 0.1 wt. % auxiliary antimicrobial agents, based upon weight of the composition.

29. The method of claim 14, wherein said polyacrylate thickener is selected from the group consisting of carbomers, acrylates/C 10-30 alkyl acrylate crosspolymers, copolymers of acrylic acid and alkyl (C5-C10)acrylate, copolymers of acrylic acid and maleic anhydride, and mixtures thereof.

30. The method of claim 14, wherein said polyacrylate thickener is a carbomer.

* * * * *